(12) United States Patent
Yu

(10) Patent No.: US 6,670,024 B1
(45) Date of Patent: Dec. 30, 2003

(54) GLASS-SILICON COLUMN

(75) Inventor: Conrad M. Yu, Oakley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/163,683

(22) Filed: Jun. 5, 2002

(51) Int. Cl.$^7$ .............................................. G01N 30/02
(52) U.S. Cl. ....................... 428/209; 428/426; 428/428; 428/432; 428/446; 428/34.4; 210/198.2; 96/101; 73/23.39
(58) Field of Search ................................ 428/426, 428, 428/446, 34.4, 209, 432; 73/23.35, 23.39; 210/198.2; 96/101

(56) References Cited

U.S. PATENT DOCUMENTS

| | | | |
|---|---|---|---|
| 6,068,780 A | * 5/2000 | Yu | 216/10 |
| 6,195,214 B1 | * 2/2001 | Muray et al. | 359/819 |

FOREIGN PATENT DOCUMENTS

| | | | | |
|---|---|---|---|---|
| JP | 60142254 A | * 7/1985 | .......... | G01N/30/60 |
| JP | 61262658 A | * 11/1986 | .......... | G01N/30/60 |
| JP | 62028664 A | * 2/1987 | .......... | G01N/30/60 |
| JP | 62108156 A | * 5/1987 | .......... | G01N/30/60 |
| JP | 63098561 A | * 4/1988 | .......... | G01N/30/02 |

* cited by examiner

*Primary Examiner*—Deborah Jones
*Assistant Examiner*—Stephen Stein
(74) *Attorney, Agent, or Firm*—Alan H. Thompson; James S. Tak

(57) ABSTRACT

A glass-silicon column that can operate in temperature variations between room temperature and about 450° C. The glass-silicon column includes large area glass, such as a thin Corning 7740 boron-silicate glass bonded to a silicon wafer, with an electrode embedded in or mounted on glass of the column, and with a self alignment silicon post/glass hole structure. The glass/silicon components are bonded, for example be anodic bonding. In one embodiment, the column includes two outer layers of silicon each bonded to an inner layer of glass, with an electrode imbedded between the layers of glass, and with at least one self alignment hole and post arrangement. The electrode functions as a column heater, and one glass/silicon component is provided with a number of flow channels adjacent the bonded surfaces.

19 Claims, 1 Drawing Sheet

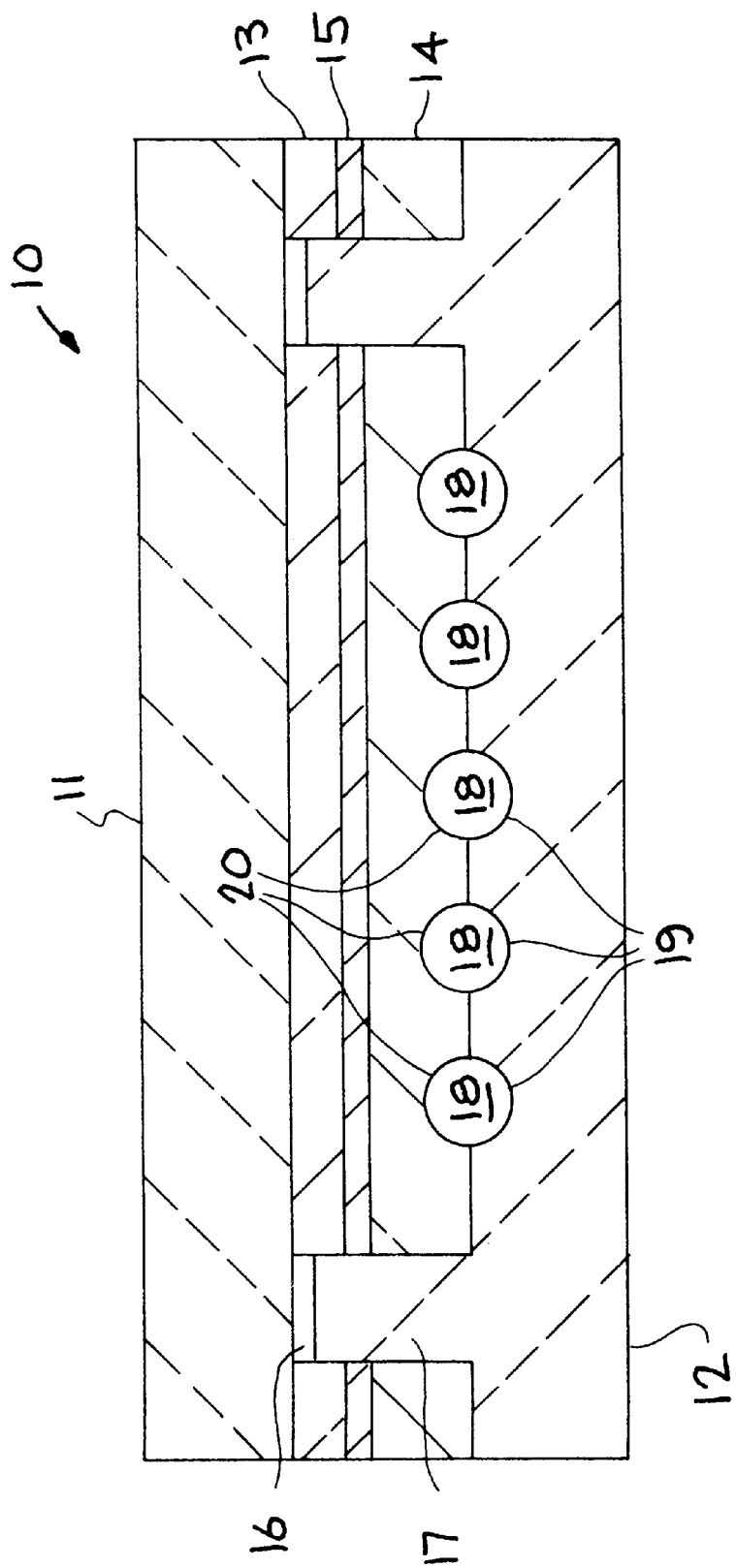

GLASS-SILICON COLUMN

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to fluid flow channels, particularly to glass/silicon fluid flow columns and more particularly to a glass-silicon column capable of use with temperatures between room temperature to about 450° C., having flow channels and an electrode embedded therein, and provided with a self-alignment silicon post and glass hole structure.

In the early 1980s, it was established that a thin piece of Corning 7740 boron silicate glass could be anodically bonded onto a silicon wafer. The glass-silicon assembly could withstand temperature variation between room temperature and about 450° C. With etched structures between the bonded glass and silicon layers or plates, they have been utilized for various applications, including coolers for many different systems.

This glass-silicon bonded system has been used in many other applications, such as where temperature variation is quite small, such as, isotherm gas chromatography, or even with small temperature ramping; electrophoresis where the applied voltage is not extremely high, and multiple channel electrolytic flow for analyzing ions or biological cells. In the gas chromatography application, the temperature of the separation column located between glass and silicon wafers, cannot vary rapidly because of the poor thermal conductivity of the glass, but its fabrication is much easier and the user can see through the glass side in case there is a blockage. In the electrophoresis application, one can even use a second piece of the thin glass with etched columns between two pieces of glass in order to be used under high voltage. The silicon wafer in this case is used to achieve more uniform temperature under heating. In the multiple channel electrolytic flow application, one can design and include various electrode and/or optical waveguide for detection and control.

The present invention provides a glass-silicon column, which can be utilized in the various above-referenced application, as well as water cooler or fluid temperature control columns for applications such as injection lasers and integrated circuit chips. The silicon wafer or layer located on opposite sides of the column of the invention achieves more uniform temperature, particularly under heating. The silicon-glass-silicon column provides are large surface area, with an electrode embedded in the glass as a column heater, but can also function as a heater for anodic bonding of the silicon and glass members or plates.

SUMMARY OF THE INVENTION

It is an object of the present invention to provide a glass-silicon column.

A further object of the invention is to provide a glass-silicon column having outer silicon layers anodically bonded to at least one inner glass layer.

Another object of the invention is to provide a glass-silicon column with at least one fluid channel therein as well as an embedded electrode.

Another object of the invention is to provide a large area silicon-glass-silicon anodically bonded column having fluid channels formed therein and an electrode embedded therein.

Another object of the invention is to provide a large area silicon-glass-silicon column with a self alignment structure for the silicon and glass members.

Another object of the invention is to provide a silicon-glass-silicon column having an embedded electrode which can function for anodic bonding of the silicon and glass as well as a column heater.

Other objects and advantages of the present invention will become apparent from the following description and accompanying drawing. The invention involves a glass-silicon column which can withstand temperature variation between room temperature and about 450° C. These variations in temperature do not cause a disruption of a large area bonding between the glass and silicon, such as between thin (10–20 Mil) Corning 7740 boron-silicate glass and a silicon wafer. The silicon wafer, in certain applications is used to achieve more uniform temperature under heating, such as by an electrode embedded in the glass. The glass-silicon column of this invention involves a large area silicon-glass-silicon column where the silicon and glass are anodically bonded. Also, the column includes an electrode which can be used for anodic bonding as well as a column heater. The silicon and glass components are provided with a self-alignment structure, such as a silicon post and a glass hole. The glass may composed of a plurality of anodically bonded layers.

BRIEF DESCRIPTION OF THE DRAWINGS

The accompanying drawing, which is incorporated into and forms a part of the disclosure, illustrates an embodiment of the invention and, together with the description, serves to explain the principles of the invention.

The single FIGURE is a cross-sectional view of an embodiment of a silicon-glass-silicon column, made in accordance with the present invention.

DETAILED DESCRIPTION OF THE INVENTION

The present invention is directed to a large area glass-silicon column, which may be, for example composed of Corning 7740 boron-silicate glass and silicon wafers or layers. The silicon and glass are anodically bonded together, and the column additionally includes an embedded electrode which can be utilized for anodic bonding and/or as a column heater. One or more fluid channels are formed in the column, and the silicon-glass assembly includes a self-alignment structure, such as one or more silicon posts which cooperate with one or more glass holes.

The illustrated and described embodiment of the glass-silicon column of this invention comprises a large area silicon-glass-silicon anodically bonded column. The area of the column, for example, is of a 3" diameter. The column includes an embedded electrode located intermediate the outer silicon layers which functions as a column heater and for anodic bonding. A plurality of fluid channels or microchannel are located intermediate the outer silicon layers or partially formed in one of the silicon layers. The column includes a self-alignment structure, composed of an alignment hole in the glass with a silicon post extending thereinto. The glass member of the column may be composed of a plurality of glass layers (10–20 Mil thick) bonded anodically, and the electrode may be embedded intermediate two of the glass layers. The outer silicon layers may, for example, have a thickness of 12 to 16 mils.

While not shown, a third glass layer with an etched column therein can be anodically bonded intermediate two glass layers bonded to the outer silicon layers.

Referring now to the drawing, the illustrated large area silicon-glass-silicon column, generally indication at 10 comprises outer silicon layers or members 11 and 12, a pair of glass layers 13 and 14 are anodically bonded to respective silicon layers 11 and 12, an electrode 15 is embedded intermediate the glass layers 13 and 14 which are anodically bonded together to form a single glass member (thickness of 20–40 Mils) with the electrode 15 embedded therein. The column includes a self-alignment structure for the silicon and glass layers and in this embodiment comprises a plurality of holes 16, only two shown, formed in glass layers 13 and 14, and a plurality of silicon posts 17, only two shown, which extend into holes 16. Note that in this embodiment of the alignment structure, the holes 16 are initially formed in both glass layers 13 and 14 (2 mm square) and the silicon posts 17 (lengths of 40 mils) are attached to or formed integral with only one silicon layer 11 or 12 and extend into the holes formed in each of the glass layers. However, the post on one end of the column could be attached to one silicon layer while the posts on the other end of the column may be attached to the opposite silicon layer. The column as illustrated in this embodiment include a plurality of fluid channels or microchannels 18 which are formed in an inner surface 19 of silicon layer or member 12 and in adjoining outer surface 20 of glass layer 14, and with the silicon/glass layers anodically bonded together, the channels 18 are leak proof from channel to channel, whereby different of fluids can pass through adjacent channels if desired. The electrode 15 may be utilized to heat the channels 18.

Since the materials of the large area column illustrated in the drawing has been experimentally shown to enable temperature variation between room temperatures and about 450 degrees C., and that these temperature variations do not cause a disruption of large area anodic bonding between silicon on glass, particularly thin Corning 7740 boronsilicate glass, the column can be utilized in many applications. For example, where temperature variation is quite small, the column can be used in isotherm gas chromatography, or even with small temperature ramping; used for temperature adjustable electrophoresis columns where the applied voltage is not extremely high; and the silicon members of the column are used to achieve more uniform temperature under heating. In addition, the column of this invention can be utilized as a water cooler for injection laser application or in the use of integrated circuit chip, as well as for electrolytic flow systems.

While a specific embodiment, materials, and parameters have been illustrated and/or described to exemplify and teach the principles of the invention, search are not intended to be limiting. Modifications and changes may become apparent to those skilled in the art, and it is intended that the invention be limited only by the scope of the appended claims.

What is claimed is:

1. A glass-silicon column, comprises a pair of outer silicon members, a glass member located intermediate the outer silicon members, an embedded electrode, at least one fluid channel, and alignment means for said silicon members and said glass member.

2. The glass-silicon column of claim 1, wherein said glass-member is composed of a plurality of bonded glass layers.

3. The glass-silicon column of claim 2, wherein said bonded glass layers are bonded by anodic bonding.

4. The glass-silicon column of claim 2, wherein said electrode is embedded intermediate two of said plurality of bonded glass layers.

5. The glass-silicon column of claim 1, wherein each of said outer silicon members are anodically bonded to said glass member.

6. The glass-silicon column of claim 1, wherein said glass member comprises a pair of anodically bonded glass layers, wherein said embedded electrode is located intermediate the pair of anodically bonded glass layers.

7. The glass-silicon column of claim 6, wherein each of said pair of anodically bonded glass layers is anodically bonded to one of said silicon members.

8. The glass-silicon column of claim 7, wherein said at least one fluid channel is located intermediate one of said pair of glass layers and an associated silicon member.

9. The glass-silicon column of claim 7, wherein said alignment means includes at least one hole in each of said of glass layers, and at least one silicon posting extending from at least one of said silicon members into said hole in each of said pair of glass layers.

10. The glass-silicon column of claim 1, wherein said alignment means includes at least one hole in said glass member, and at least one silicon post extending from at least one of said silicon members into said at least one hole.

11. The glass-silicon column of claim 1, wherein said at least fluid channel is located partially in an inner surface of one of said silicon members and partially in an adjacent outer surfaces of said glass member.

12. The glass-silicon column of claim 1, wherein said electrode comprises a heater for said column.

13. The glass-silicon column of claim 12, wherein said electrode additionally function for anodic bonding of components of the column.

14. A silicon-glass-silicon column comprising:

a first outer silicon member, at least one glass member, a second outer silicon member, an electrode embedded in said glass member, at least one flow-channel intermediate said glass member and one of said silicon members, and a self-alignment structure located intermediate said first and second silicon members.

15. The column of claim 14, wherein said at least one glass member is anodically bonded to each of said silicon members.

16. The column of claim 14, wherein said at least one glass member is composed of a plurality of glass members anodically bonded together.

17. The column of claim 16, wherein said electrode is located intermediate a pair of said plurality of glass members.

18. The column of claim 14, wherein said electrode is constructed to provide heat for anodic bonding of the column components and for providing heat for at least one fluid channels.

19. The column of claim 14, wherein said glass member is composed of a plurality of glass layers anodically bonded together, with each glass layer having a thickness of 10–20 mils.

\* \* \* \* \*